United States Patent
O'Lenick et al.

(10) Patent No.: US 8,623,342 B1
(45) Date of Patent: *Jan. 7, 2014

(54) NATURALLY DERIVED CITRATE POLYESTERS

(75) Inventors: Kevin A. O'Lenick, Dacula, GA (US);
Andrew J. O'Lenick, Dacula, GA (US);
Anthony J. O'Lenick, Jr., Dacula, GA (US)

(73) Assignee: SurfaTech Corporation, Lawrenceville, GA (US)

( * ) Notice: Subject to any disclaimer, the term of this patent is extended or adjusted under 35 U.S.C. 154(b) by 233 days.

This patent is subject to a terminal disclaimer.

(21) Appl. No.: 13/374,186

(22) Filed: Dec. 16, 2011

Related U.S. Application Data

(63) Continuation-in-part of application No. 12/584,274, filed on Sep. 3, 2009.

(60) Provisional application No. 61/271,259, filed on Jul. 20, 2009.

(51) Int. Cl.
*A61K 8/72* (2006.01)
*A61K 8/85* (2006.01)
*A61Q 5/12* (2006.01)
*C08G 63/60* (2006.01)

(52) U.S. Cl.
CPC ... *A61K 8/85* (2013.01); *A61Q 5/12* (2013.01); *C08G 63/60* (2013.01)
USPC ..................................... 424/70.11

(58) Field of Classification Search
None
See application file for complete search history.

(56) References Cited

U.S. PATENT DOCUMENTS

| | | | | |
|---|---|---|---|---|
| 2,122,716 | A | * | 7/1938 | Graves .................... 560/179 |
| 4,868,236 | A | * | 9/1989 | O'Lenick, Jr. ............. 524/308 |
| 5,089,658 | A | | 2/1992 | Elmore |
| 8,148,569 | B1 | * | 4/2012 | O'Lenick et al. ........... 560/146 |
| 2007/0098666 | A1 | * | 5/2007 | Behler et al. ............. 424/70.31 |

OTHER PUBLICATIONS

Bujans et al., Revista CENIC, Ciencias Quimicas, 2000, 31(3), pp. 165-169.*

* cited by examiner

*Primary Examiner* — Brian Gulledge

(57) ABSTRACT

The present invention is directed to a series of polymeric citrate esters that has very unique rheology properties. These materials find applications as additives to formulations in personal care products where there is a desire to have a structured film and flow properties. These compounds by virtue of their unique structure provide outstanding skin feel and outstanding waterproof properties in cosmetic formulations most notable sunscreens.

3 Claims, No Drawings

NATURALLY DERIVED CITRATE POLYESTERS

RELATED APPLICATIONS

This application is a continuation in part of Ser. No. 12/584,274, filed Sep. 3, 2009, which claims priority to and benefit of U.S. Provisional Application No. 61/271,259 filed Jul. 20, 2009, the disclosure of which is incorporated herein for all purposes.

FIELD OF THE INVENTION

The present invention is directed to a series of polymeric citrate esters that have two different molecular weight ester chains, one solid and one liquid, which when combined into a single molecule make a polymer that is solid, but has very unique flow properties. These materials find applications as additives to formulations in personal care products where there is a desire to have a structured film (provided by the solid fatty group) and flow properties, (provided by the liquid fatty group). These compounds by virtue of their unique structure provide outstanding skin feel.

BACKGROUND OF THE INVENTION

Citric acid is a common material of natural origin. The structure is:

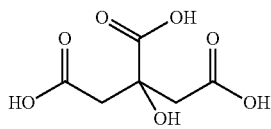

CAS Registry Number: 77-92-9
CA Index Name: 1,2,3-Propanetricarboxylic acid, 2-hydroxy- Citric acid is made by fermentation, using cultures of *Aspergillus niger* are fed on a sucrose or glucose-containing medium.

Citric acid is one of a series of compounds involved in the physiological oxidation of fats, proteins, and carbohydrates to carbon dioxide and water. This series of chemical reactions is central to nearly all metabolic reactions, and is the source of two-thirds of the food-derived energy in higher organisms. Krebs received the 1953 Nobel Prize in Physiology or Medicine for the discovery. The series of reactions is known by various names, including the citric acid cycle, the Krebs cycle, and the tricarboxylic acid cycle Citrate esters are known. They conform to the following structure:

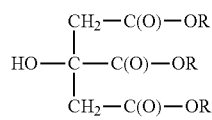

The esters are made by the reaction of fatty alcohols with citric acid.

U.S. Pat. No. 4,292,192 issued to Hooper, et al. teaches that Detergent bars for personal washing are given a deodorant property by including an ester of citric acid. The ester may be an acetyl derivative. The amount of ester used will be in the range of from about 0.3% to about 3%. Examples of the esters are triethyl citrate and acetyl tributyl citrate.

U.S. Pat. No. 2,122,716 describes long chain esters of citric acid, e.g., tridodecyl citrate, which have been used as plasticizers for resinous compositions.

U.S. Pat. Nos. 3,239,555 and 3,241,992 disclose bis-citric acid esters made by esterifying the acid groups with C1 to C18 alcohols and coupling the esters with dibasic acids. Such esters are useful as plasticizers for plastics.

U.S. Pat. No. 3,251,792, the acid groups of citric acid are esterified with alkyl, aryl, cycloalkyl and haloaryl alcohols and the hydroxyl group is esterified with a carbonyl compound. Such compounds are used as stabilizers for polypropylene.

U.S. Pat. No. 4,868,236 to O'Lenick discloses a guerbet citric ester and polymers thereof useful in plastic lubrication.

None of these patents provide polyester derivatives of mixed fatty esters of citrate as envisioned by the present invention.

The compounds of the present invention provide outstanding waterproofing properties on skin as well as emolliency.

THE INVENTION

Objective of the Invention

The present invention has as its objective a series of citrate polyesters that have fatty groups contained thereon and are crosslinked by diols and contain fatty groups, one solid at room temperature, the other liquid at room temperature.

The present invention also has an objective a process for treating hair and skin with the citrate polyesters that have fatty groups contained thereon and are crosslinked by the diol.

Other objectives will become clear as one reads the specification and claims herein.

SUMMARY OF THE INVENTION

The present invention discloses a polyester made by the reaction of fatty acids reacted with citric acid and a diol crosslinker.

DETAILED DESCRIPTION OF THE INVENTION

The present invention relates to a polyester that conforms to the following structure:

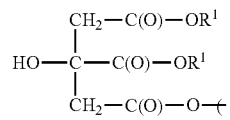 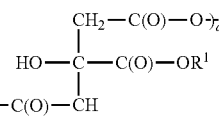 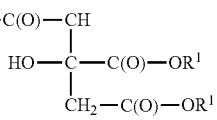

$R^1$ is $-(CH_2)_b-CH_3$;

b is an integer ranging from 11 to 31 or mixtures thereof;
$R^2$ is —$(CH_2)_3$—;
a is an integer ranging from 0 to 20.

Another aspect of the present invention is a process for conditioning hair and skin which comprises contacting the hair or skin with an effective conditioning concentration of a polyester that conforms to the following structure:

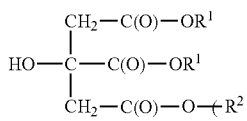 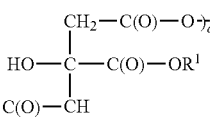 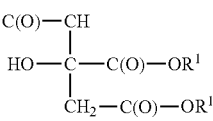

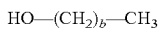

b is an integer ranging from 6 to 31;
$R^2$ is —$(CH_2)_3$—;
a is an integer ranging from 0 to 20.

In a preferred embodiment said effective conditioning concentration ranges from 0.1% to 20% by weight.

The products of the present invention are made by the esterification reaction of:
(a) citric acid conforming to the following structure:

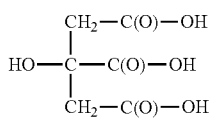

(b) HO—$(CH_2)_3$—OH, a natural diol made from corn;
(c) a fatty alcohol conforming to the following structure:

b is an integer ranging from 6 to 31 or mixtures thereof.

Another aspect of the present invention is a process for conditioning hair and skin which comprises contacting the hair or skin with an effective conditioning concentration of a polyester made by the esterification reaction of:
(a) citric acid conforming to the following structure:

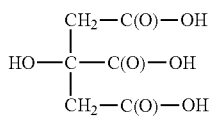

(b) HO—$(CH_2)_3$—OH, a natural diol made from corn;
(c) a fatty alcohol conforming to the following structure:

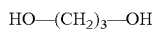

b is an integer ranging from 6 to 31 or mixtures thereof.

Where there are two different types of ester group present, one liquid (C6-C10) and one solid (C12-C31), the resulting structure cannot crystallize completely, since the liquid domains in the polymer act as molecular crystal distorters, resulting in a polymer that although having the same melting point, flows more easily when pressure is applied. The resulting solid will be soft and flowable, rather than hard and un-yielding.

PREFERRED EMBODIMENTS

In a preferred embodiment a is an integer ranging from 1 to 20.

In a preferred embodiment a is an integer ranging from 3 to 10.

In a preferred embodiment a is 10.

In a preferred embodiment a is 15.

In a preferred embodiment 10 said effective conditioning concentration ranges from 0.1% to 20% by weight.

In a preferred embodiment $R^1$ is alkyl having 6 to 20 carbon atoms.

In a preferred embodiment $R^1$ is alkyl having 8 to 12 carbon atoms.

In a preferred embodiment $R^1$ is alkyl is alkyl having 6 to 8 carbon atoms.

In a preferred embodiment $R^1$ is alkyl is alkyl having 10 to 20 carbon atoms.

In a more preferred embodiment $R^1$ is a mixture of alkyl one group having 8 to 10 carbon atoms and the second having 18 to 24 carbon atoms.

EXAMPLES

Example 1

Citric Acid

Citrate is an item of commerce commercially available from a variety of sources including Pfizer. It conforms to the following structure:

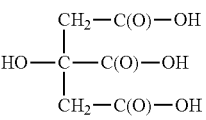

Example 2

1,3 Propane Diol 1,3 propane diol is a natural product derived from corn. DuPont Tate & Lyle Bio Products' 1,3-propanediol is a colorless and highly pure glycol derived from a sustainable and renewable corn sugar fermentation process. Corn-derived 1,3-propanediol is the perfect glycol solution for formulations and ingredient solvents where non-petroleum based ingredients are desired, and can replace propylene glycol and butylene glycol. Benefits of corn-derived 1,3-propanediol include its purity, lack of irritation and sensitization, and environmentally friendly nature. This natural diol conforms to the following structure:

HO—$(CH_2)_3$—OH

In the present invention this material provides a linking group that is (a) natural, (b) free of polyoxyethylene and polyoxypropylene compounds and their inherent ether groups and lack of natural origin, and (c) are easily reacted into the polymer matrix.

Examples 3-21

Fatty Alcohols

These acids are an item of commerce available from a variety of sources. It conforms to the following structure;

HO—(CH$_2$)$_b$—CH$_3$ b is an integer ranging from 11 to 31.

Fatty alcohols commercially available from a variety of sources including Condea.

| Ex | IUPAC name | Common name | CAS registry number | Molecular formula | MW |
|---|---|---|---|---|---|
| In this table "b" is calculated as the number of carbon atoms −1. ||||||
| 3 | 1-Hexanol | Caproic alcohol | 111-27-3 | C$_6$H$_{14}$O | 102.2 |
| 4 | 1-Heptanol | enanthic alcohol | 111-70-6 | C$_7$H$_{16}$O | 116.2 |
| 5 | 1-Octanol | Caprylic alcohol | 111-87-5 | C$_8$H$_{18}$O | 130.2 |
| 6 | 1-Nonanol | Pelargonic alcohol | 143-08-8 | C$_9$H$_{20}$O | 144.3 |
| 7 | 1-Decanol | capric alcohol | 112-30-1 | C$_{10}$H$_{22}$O | 158.3 |
| 8 | 1-Undecanol | | 112-42-5 | C$_{11}$H$_{24}$O | 172.3 |
| 9 | 1-Dodecanol | lauryl alcohol | 112-53-8 | C$_{12}$H$_{26}$O | 186.3 |
| 10 | 1-Tridecanol | | 112-70-9 | C$_{13}$H$_{28}$O | 200.4 |
| 11 | 1-Tetradecanol | myristyl alcohol | 112-72-1 | C$_{14}$H$_{30}$O | 214.4 |
| 12 | 1-Pentadecanol | | 629-76-5 | C$_{15}$H$_{32}$O | 228.4 |
| 13 | 1-Hexadecanol | cetyl alcohol | 36653-82-4 | C$_{16}$H$_{34}$O | 242.5 |
| 14 | 1-Heptadecanol | margaryl alcohol | 1454-85-9 | C$_{17}$H$_{36}$O | 256.5 |
| 15 | 1-Octadecanol | stearyl alcohol | 112-92-5 | C$_{18}$H$_{38}$O | 270.5 |
| 16 | 1-Nonadecanol | | 1454-84 | C$_{19}$H$_{40}$O | 284.5 |
| 17 | 1-Eicosanol | arachidyl alcohol | 629-96-9 | C$_{20}$H$_{42}$O | 298.6 |
| 18 | 1-Heneicosanol | | 15594-90-8 | C$_{21}$H$_{44}$O | 312.6 |
| 19 | 1-Docosanol | behenyl alcohol | 661-19-8 | C$_{22}$H$_{46}$O | 326.6 |
| 20 | 1-Tricosanol | | 3133-01-5 | C$_{23}$H$_{48}$O | 340.6 |
| 21 | 1-Tetracosanol | Lignoceryl alcohol | 506-51-4 | C$_{24}$H$_{50}$O | 354.7 |

To a suitable reactor equipped with heating and an ability to distill off water is added the specified number of grams of citrate acid (Example 1), next is added the specified number of grams of the fatty alcohol (Examples 3-21). The reaction mass is heated to 150-160° C. and water is distilled off. As the reaction proceeds, the batch clears and free citric acid is reacted out. The reaction mass is kept at this temperature until the acid value becomes vanishingly low. Next is added the specified number of grams of the specified 1,3 propane diol (Examples 2). The reaction mass is heated to 180-190° C. and water is distilled off. The reaction mass is kept at this temperature until the acid value becomes vanishingly low. The reaction mass is cooled and used without additional purification.

| Example | Example 1 Citric Acid Grams | Example 2 Diol Grams | Alcohol Example | Alcohol Grams | "a" |
|---|---|---|---|---|---|
| 25 | 384 | 76 | 6 | 408 | 0 |
| 26 | 1344 | 456 | 7 | 1044 | 5 |
| 27 | 2304 | 836 | 8 | 1820 | 10 |
| 28 | 3264 | 1216 | 9 | 2736 | 15 |
| 29 | 4224 | 1596 | 10 | 3792 | 20 |
| 30 | 384 | 76 | 11 | 688 | 0 |
| 31 | 1344 | 456 | 12 | 1674 | 5 |
| 32 | 2304 | 836 | 13 | 2800 | 10 |
| 33 | 3624 | 1216 | 14 | 4066 | 15 |

-continued

| Example | Example 1 Citric Acid Grams | Example 2 Diol Grams | Alcohol Example | Alcohol Grams | "a" |
|---|---|---|---|---|---|
| 34 | 4224 | 1596 | 15 | 5472 | 20 |
| 35 | 384 | 76 | 16 | 968 | 0 |
| 36 | 1344 | 456 | 17 | 2304 | 5 |
| 37 | 2304 | 836 | 18 | 3780 | 10 |
| 38 | 3264 | 1216 | 19 | 5396 | 15 |
| 39 | 4224 | 1596 | 20 | 7152 | 20 |
| 40 | 384 | 76 | 21 | 1248 | 0 |
| 41 | 1344 | 456 | 22 | 2934 | 5 |
| 42 | 2304 | 836 | 23 | 4760 | 10 |
| 43 | 3264 | 1216 | 24 | 6783 | 15 |

Ex means example in the table above.

Products that are of the present invention were low order soft pastes that liquefied under pressure. Those products that were made using only solid fatty acids were hard solids that were not spreadable on the skin or hair. Those made without solid fatty acids, but only liquid fatty acids, (oleic and iso stearic) were sticky liquids. Those made with iso-stearic acid were glossy on hair and skin, while those made with oleic acid were emollients.

The compounds are of exceptional interest in the personal care applications where gloss, rheology that accommodates spreading and odor are critical.

The compounds of the present invention in addition to their unique aesthetics are surprisingly water proofing agents when used in cosmetic formulations, most importantly sunscreens.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed:

1. A polyester made by the esterification reaction of:

(a) citric acid conforming to the following structure:

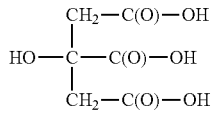

(b) HO—(CH$_2$)$_3$—OH, and (c) a fatty alcohol conforming to the following structure:

HO—(CH$_2$)$_b$—CH$_3$ b is an integer ranging from 6 to 31 or mixtures thereof.

2. A process for conditioning hair and skin which comprises contacting the hair or skin with an effective conditioning concentration of a polyester made by the esterification reaction of:

(a) citric acid conforming to the following structure:
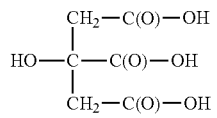
(b) HO—(CH$_2$)$_3$—OH, and
(c) a fatty alcohol conforming to the following structure;
b is an integer ranging from 6 to 31 or mixtures thereof.
3. A process of claim 2 wherein said effective conditioning concentration ranges from 0.1% to 20% by weight.
* * * * *